United States Patent
Gailius et al.

(10) Patent No.: US 9,696,291 B2
(45) Date of Patent: Jul. 4, 2017

(54) ELECTRONIC NOSE FOR DETERMINATION OF MEAT FRESHNESS

(71) Applicants: KAUNAS UNIVERSITY OF TECHNOLOGY, Kaunas (LT); UAB Ars Lab, Vilnius (LT)

(72) Inventors: Darius Gailius, Kaunas (LT); Rimanté Vinauskiené, Kaunas (LT); Augustas Alešiūnas, Vilniaus raj. (LT); Gediminas Kvaraciejus, Vilniaus raj. (LT)

(73) Assignees: KAUNAS UNIVERSITY OF TECHNOLOGY (LT); UAB "ARS LAB" (LT)

( * ) Notice: Subject to any disclaimer, the term of this patent is extended or adjusted under 35 U.S.C. 154(b) by 0 days.

(21) Appl. No.: 14/376,939

(22) PCT Filed: Jun. 18, 2014

(86) PCT No.: PCT/IB2014/062356
§ 371 (c)(1),
(2) Date: Aug. 6, 2014

(87) PCT Pub. No.: WO2015/150880
PCT Pub. Date: Oct. 8, 2015

(65) Prior Publication Data
US 2016/0161461 A1     Jun. 9, 2016

(30) Foreign Application Priority Data

Apr. 1, 2014 (LT) ..................................... 2014 055

(51) Int. Cl.
*G01N 33/12* (2006.01)
*G01N 33/00* (2006.01)

(52) U.S. Cl.
CPC ......... *G01N 33/12* (2013.01); *G01N 33/0031* (2013.01); *G01N 33/0047* (2013.01); *G01N 33/0054* (2013.01)

(58) Field of Classification Search
CPC .. G01N 33/212; G01N 33/12; G01N 33/0047; G01N 33/0054
(Continued)

(56) References Cited

U.S. PATENT DOCUMENTS

| 4,980,294 A * | 12/1990 | Elias ..................... G01N 33/12 426/231 |
| 2006/0078658 A1 * | 4/2006 | Owens .................... G01N 1/24 426/231 |

(Continued)

FOREIGN PATENT DOCUMENTS

| CN | 101493431 | 7/2009 |
| CN | 101806741 | 8/2010 |

(Continued)

OTHER PUBLICATIONS (Huang, Lin, Nondestructive Measurement of Total Volatile Basic Nitrogen (TVB-N in Pork Meat by Integrating Near Infrared Spectroscopy, Computer Vision and Electronic Nose Techniques, Food Chemistry Jun. 25, 2013.*

(Continued)

*Primary Examiner* — Harshad R Patel
*Assistant Examiner* — Monica S Young
(74) *Attorney, Agent, or Firm* — Hershkovitz & Associates, PLLC; Abe Hershkovitz (57) ABSTRACT

The invention relates to a new and fast device for determination of freshness of the food of animal origin, specifically to the electronic nose, to a method for determination of freshness of the food by using a portable electronic nose which analyses volatile compounds and gases in the meat (Continued)

E-Nose headspace, and to a system that includes the electronic nose and the tool for shielding extraneous odors and forming the defined headspace. The invention describes a fast and simple method for determination of the meat freshness, which is easy to use and the results get by it are objective and reliable.

12 Claims, 8 Drawing Sheets

(58) Field of Classification Search
USPC .............................................................. 73/23
See application file for complete search history.

(56) References Cited

U.S. PATENT DOCUMENTS

| | | | | |
|---|---|---|---|---|
| 2008/0299669 | A1* | 12/2008 | Lavigne | G01N 21/77 |
| | | | | 436/111 |
| 2009/0084162 | A1* | 4/2009 | Besnard | G01N 27/127 |
| | | | | 73/31.06 |
| 2012/0028820 | A1* | 2/2012 | Rhodes | B82Y 15/00 |
| | | | | 506/9 |
| 2014/0007652 | A1* | 1/2014 | Tomic Stefanin | G01N 1/22 |
| | | | | 73/23.41 |
| 2014/0162893 | A1* | 6/2014 | Cash | G01N 33/5438 |
| | | | | 506/9 |
| 2016/0116434 | A1* | 4/2016 | Mwakikunga | G01N 27/4141 |
| | | | | 257/253 |

FOREIGN PATENT DOCUMENTS

| | | |
|---|---|---|
| CN | 10232367 | 1/2012 |
| KR | 20120049729 | 5/2012 |
| RU | 2239829 | 11/2004 |

OTHER PUBLICATIONS (Rajamaki, Tiina "Application of an Electronic Nose for Quality Assessment of Modified Atmosphere Packaged Poultry Meat" Science Direct, Nov. 8, 2003.*
Hasan N ul, Ejaz N, Ejaz W, Kim HS. Meat and Fish Freshness Inspection System Based on Odor Sensing. Sensors (Basel, Switzerland). 2012;12(11):15542-15557. doi:10.3390/s121115542.*

* cited by examiner

Fig. 1. Output signals of the e-nose sensors (solid line - for ammonia (NH$_3$), dashed line - for hydrocarbons (CH)) after switching-on (from 0 second) in the air and above four meat samples of different quality.

Fig. 2. Variation of output signals of the e-nose sensors after the sudden increase in concentration of the 'sniffed' gas mixture. Output voltages of CH and NH$_3$ sensors.

Fig. 3. Variation of output signals of the e-nose sensors after the sudden decrease in concentration of the 'sniffed' gas mixture. Output voltages of the CH and $NH_3$ sensors.

Fig. 4. Variation of output signals of the sensors after the placement of the e-nose sensors into the cylindrical (10 cm diameter) container of 1-litre capacity with the chicken meat inside. Up to the 220th second the container remains covered with a lid, then the lid is removed. Output voltages of the CH and $NH_3$ sensors.

Fig. 5. Variation of output signals of the sensors when the chicken meat is stored at room temperature (rationed voltages of the sensor output). Output voltages of the CH and $NH_3$ sensors.

The spoiling chicken exudes more than 100 volatile substances. In such a complex 'bouquet' of odours it is very difficult and expensive to determine the concentrations of the individual compounds (e.g. gas chromatography and spectrometry).

Fig. 6. CH sensor voltage dependence on the concentration of standard carboxylic acid solutions Fig. 7. Variations in carboxylic acid during storage Fig. 8. Variations in carboxylic acid at the spoilage phase Fig. 9. Variations in CH sensor voltage during storage Fig. 10. Dependence between the CH sensor voltage and carboxylic acid content during storage of the poultry Fig. 11. Dependence between the NH$_3$ sensor voltage and carboxylic acid content during storage of the poultry

Fig. 12

Fig. 13. Key Diagram of the E-nose

Fig. 14. Operating Diagram of the E-nose

FIG. 15  E-Nose

ELECTRONIC NOSE FOR DETERMINATION OF MEAT FRESHNESS

FIELD OF TECHNOLOGY

The invention relates to a new and fast method for determination of freshness of the food of animal origin which analyses volatile compounds and gases in the meat headspace by using a portable electronic nose.

STATE OF THE ART

Currently, a supplier or seller is usually responsible for quality of the fresh meat, and a buyer usually assesses freshness of the meat visually. As we know, the meat while losing its freshness and spoiling gets an odour of certain intensity, as it exudes certain volatile substances. In meat processing plants, the meat of suspicious freshness is checked in laboratories, but individual users are not able to do it quickly. Organoleptic and histological assessment methods, as well as chemical and microscopic analysis are mainly used for assessment of the meat quality. However, some of these methods are subjective (organoleptic assessment method), the others are rather complicated (chemical and microscopic analysis). In many cases, biological testing equipment and professionals are required, and the testing itself takes at least 2-3 days.

As for the average consumer, an inapplicable solution is to sniff the meat each time to check its freshness, there is a necessity for creation of a mobile device which immediately assesses the meat freshness and provides the data.

Patent CN101806741 describes a quick method and device for determination of meat freshness based on electrochemical luminescence. The purpose of the invention is achieved by using iridium, platinum, silver electrodes, when the ammonia produced meat can be constantly found in the decaying meat. The device is of a lightweight construction, cheap and can be used for quick determination of the meat freshness. However, a drawback of this invention is a narrow range of the substances found, while there is a significant content of volatile substances produced in the spoiling material.

Patent RU2239829 describes a method for determination of the meat freshness, where the sample taken out of the product is extracted, centrifuged, and boiled-off; the subsequent chromatographic separation and Scion Image computer analysis provide the data about the concentration of biogenic amines; the latter parameter is taken as a basis to assess the degree of the meat freshness. However, this invention can be applied for determination of the meat freshness under laboratory conditions and in production.

There is known patent CN102323267 which describes a system and method for quick assessment of freshness of the raw meat. The invention describes a system which consists of: a video spectrometer, a CCD digital camera, a direct current light source, a light source stabilizing device, a camera controller, a computer and an image collecting chip, and a method for determination of the meat freshness by using the spectral image capture of the meat surface, assessment of the meat freshness and determination of its degree according to physical and chemical parameters, analysis of the results obtained by using the mathematical methods, as well as the development of the model for assessment of the meat freshness. A drawback of this invention is that it is a stationary device and the freshness parameters are determined by the volatile nitrogen, pH value and colour.

There is known patent KR20120049729, which describes a device and method for determination of freshness of the packaged meat. The apparatus comprises a meat sample injection device, a surface sensor which is designed to detect the gas emitted from the injected sample, an analyser, a computer, a device for determining the concentration of the detected gas, and a device for final determination of the meat freshness. However, it is a stationary device, thus hinders quick determination of the meat freshness.

It is known patent CN101493431, which describes a method of the use of an electronic nose for determination of the chicken meat freshness, where a chicken sample is heated to a certain temperature in a container with a thermostatic control, after which the sample is analysed by output signal values of each sensor. The described determination method is more complicated and measured by other parameters.

All of the above-described methods for determination of the meat freshness require preparation, are inconvenient for use and expensive, they take time or need professional performance.

Essence of the Invention

Main precursors of the meat odour are water- or fat-soluble compounds, from which an odour of the meat products forms during the further technological process. It is supposed that the main water-soluble odour precursors are carbohydrates and their phosphates, free amino acids, peptides, nucleotides, and other nitrogen-containing compounds, for example, triethylamine.

Volatile compounds form and accumulate during the autolysis and further spoilage when proteins and peptides fission. Deamination of amino acids and their amides produces volatile acids (formic, acetic, butyric, propionic, caproic, valerian, etc.) and increases contents of other organic acids (lactic, pyruvic, etc.) and carbonyl compounds (aldehydes, ketones). During spoilage of the meat, the bacteria growing in tissues release ammonia, amines and volatile sulphur compounds, hydrocarbons, alcohols, aldehydes, ketones, esters, acetone and low-molecular-weight carboxylic acids. Under anaerobic conditions a malodorous phosphine ($PH_3$) forms.

Release of the odour compounds from the food matrix is influenced by the physico-chemical interaction between the volatile odour compounds and food ingredients, as well as characteristics of the food structure.

Concentration of the release of volatile compounds from one phase to another depends on the temperature, food composition, structure, viscosity in different phases, molecular interactions (with proteins, lipids, carbohydrates) and reversible interactions (hydrophobic interactions between the odour compounds, such as esters and proteins). Dissemination of volatile compounds in the environment depends on conditions of the surrounding environmental, air movement parameters; and in the case of the stable headspace a smell of a product is disseminated in the least.

The purpose of the invention is to create a portable electronic nose, which can help a user quickly determinate freshness of the meat. The invention describes a fast and simple method for determination of the meat freshness, which is easy to use and the results get by it are objective and reliable.

The electronic nose described in the invention is designed for the determination of odours and volatile components, analysis and final determination of the freshness. This electronic nose, comparing with the known methods for determination of freshness, accurately and quickly assesses and presents the meat freshness result, so we think that it will be widely applied in daily consumption.

THE MOST SUITABLE OPTIONS FOR IMPLEMENTATION

The most appropriate way to assess quality of the fresh meat is analysing the gaseous substances of the headspace of a sample. Metal-oxide-semiconductor (MOS) sensors of the new generation were used as gas sensors for the device developed, as their technology is widely researched, and there is possibility in the market to purchase commercially manufactured sensors, which are optimized for detection of various gases and measurement of its concentration. Most types of gas sensors are sensitive not to one particular gas, but to the whole bouquet of the allied gases, therefore experimental research were carried out.

After having measured voltage $V_{RL}$, a resistance of the sensor-sensitive layer can be calculated using the following formula (1):

$$Rs = R_L \cdot \left(\frac{V_C}{V_{RL}} - 1\right) \quad (1)$$

The following metal oxide MOS sensors of a new type are used in the device of the invention: CH (VOC-volatile organic compounds) and $NH_3$ (ammonia) sensors that react differently to various concentrations of all volatile organic compounds in and their variations. Variation in gas sensor output signals means the detected/recorded different concentration of volatile organic compounds and hydrocarbons in the headspace of the meat tested. These signals are transmitted to the processor in the e-nose and are transmitted via a Bluetooth-type device or USB ports to mobile devices with special software, which, according to the algorithms provide the result to user: "Fresh", "Unsafe" or "Spoiled". In the invention to be patented, the most appropriate way to assess quality of the fresh meat is analysing the gaseous substances and volatile compounds of the headspace of a sample, and measuring the gas concentration.

An electronic nose laboratory device was created, and it includes a metal-oxide-sensor system adapted to respond to the speed of changes in the concentration of volatile compounds, a processor, which is designed to receive and process signals incoming from the sensor system and turn them into a sequence of electrical signals on the basis of variation in the concentration of volatile compounds, a Bluetooth-type device or USB ports, which transmit signals to mobile devices with special software, which, according to the algorithms in synchronisation with the cloud, provides the user result of the meat tested.

A tool shielding extraneous odours and creating a defined headspace is used as an option, and it includes a container with a lid, a cover or a funnel tip-cover to isolate sensors from the environment gases.

While measuring in the open space of the sample over the meat, a distance from the sensors to the surface of the meat has to be less than 10 mm.

MOS gas sensors for hydrocarbons and ammonia can detect most efficiently the volatile organic compounds released during the meat spoilage. CH and $NH_3$ sensors were chosen as the main e-nose sensors.

In order to create an e-nose, which can present measurement results as soon as possible, durations of the calibration processes (preferably, as low as possible) are important:
  having switched-on the sensor power supply;
  variations and speed of the sensor output signals after sudden changes in gas concentrations.

While different MOS sensors are optimized for measurement of concentration of a certain gas, but they respond to other gases as well (cross sensitivity).

In order to reduce an influence of the convection and diffusion and to assess concentration levels of volatile compounds more reliably, stability of the sample headspace needs to be ensured. This can be done in the simplest way by placing a sample into a covered container and holding it for several minutes.

Figure 1:
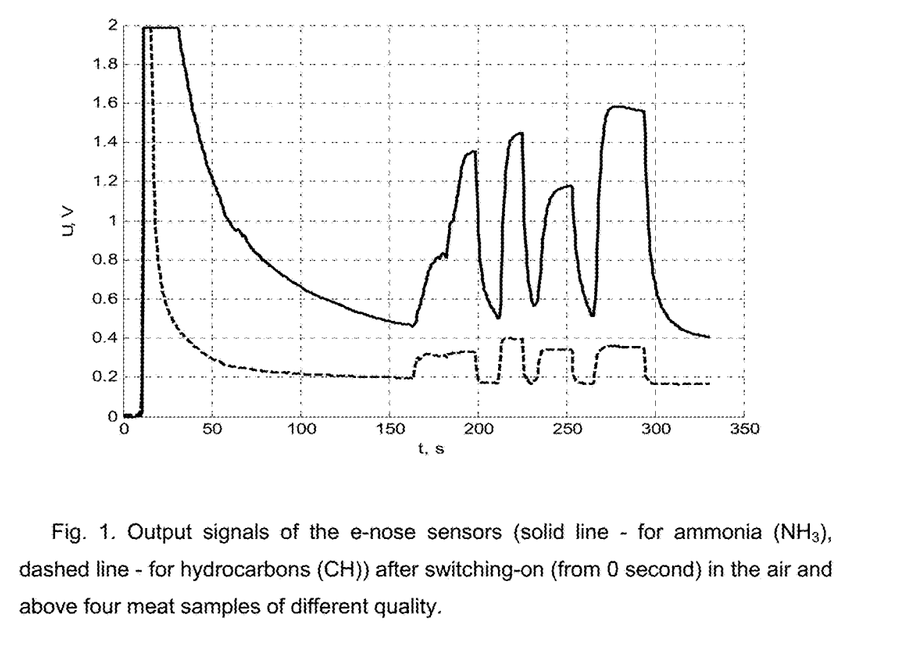
FIG. 1. Output signals of the e-nose sensors after switching-on (from 0 second) in the air and above four meat samples of different quality.
Figure 2:
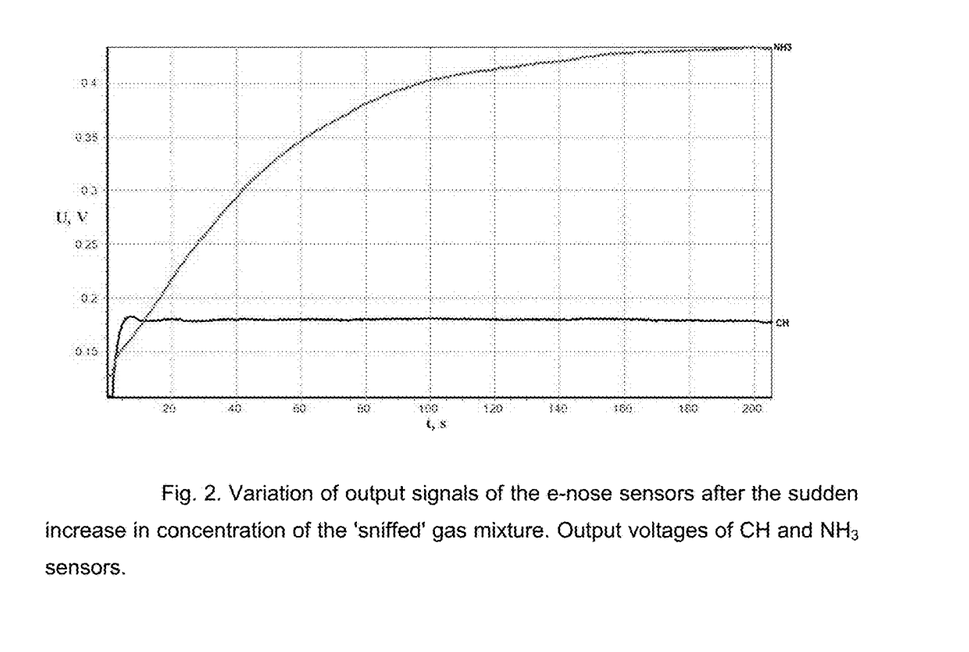
FIG. 2. Variation of output signals of the e-nose sensors after the sudden increase in concentration of the 'sniffed' gas mixture.
Figure 3:
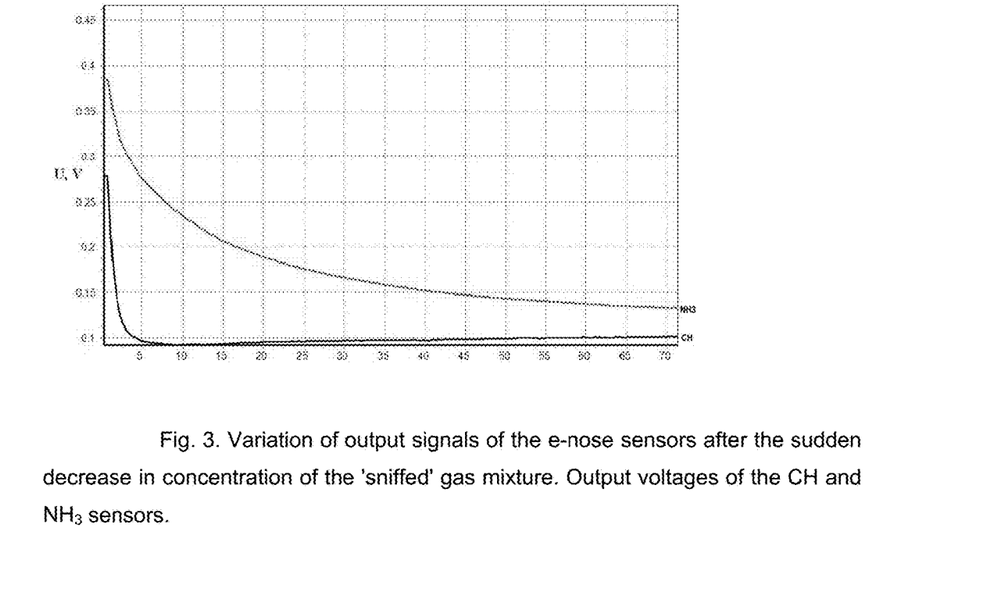
FIG. 3. Variation of output signals of the e-nose sensors after the sudden decrease in concentration of the 'sniffed' gas mixture.
Figure 4:
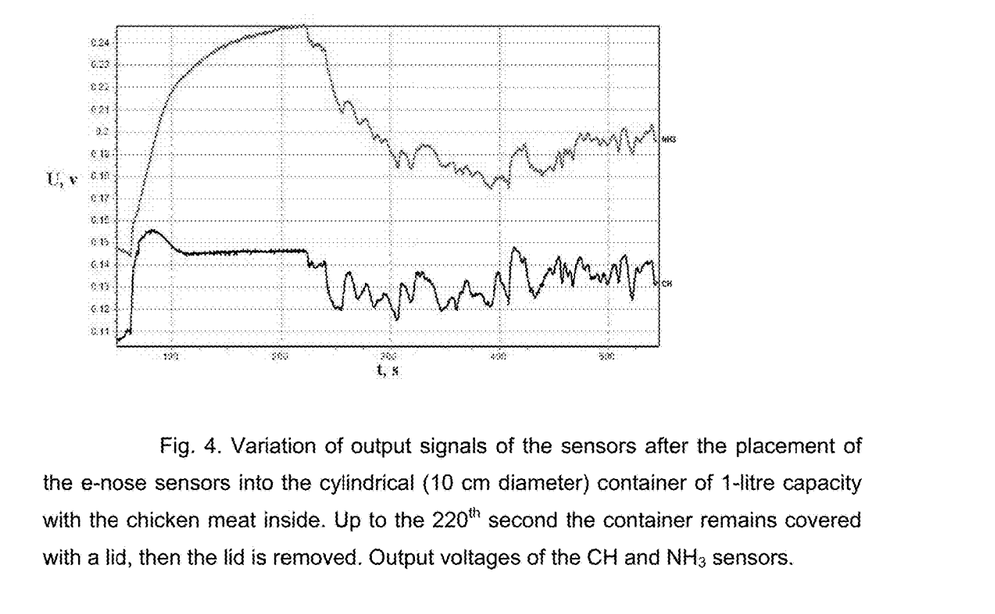
FIG. 4. Variation of output signals of the sensors after the placement of the e-nose sensors into the cylindrical (10 cm diameter) container of 1-liter capacity with the chicken meat inside.
Figure 5:
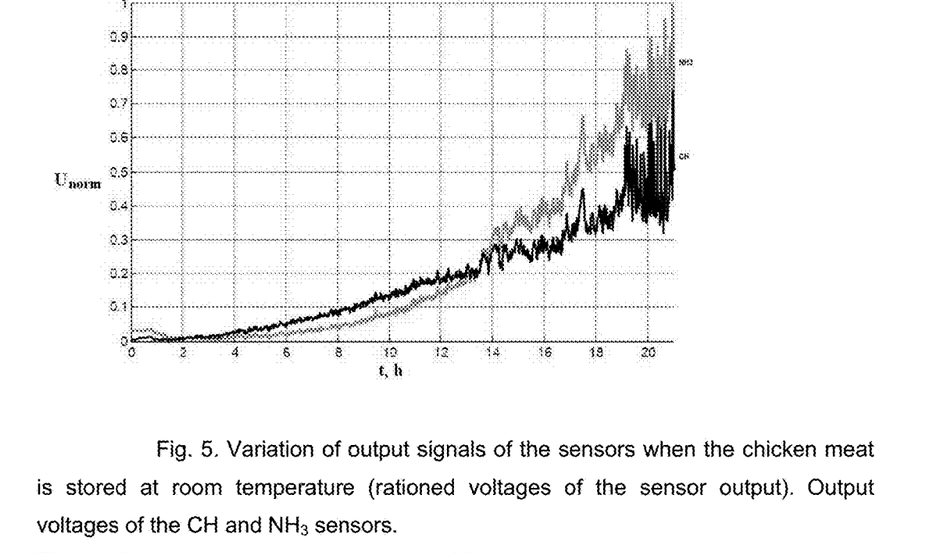
FIG. 5. Variation of output signals of the sensors when the chicken meat is stored at room temperature (rationed voltages of the sensor output).

FIG. 4 and FIG. 5 provide examples of the measurement results, where a prototype of the e-nose is used, when a covered container (more stable headspace) and an open container are sniffed.

As is apparent from the case of the uncovered container, a concentration of volatile compounds varies considerably.

Compounds forming the chicken odour are saturated and unsaturated aldehydes and ketones, alcohols and their isomers, alkanes, terpenes, sulphur-containing compounds, aromatic compounds, carboxylic acids and other compounds. The most commonly detected compounds are as follows: 2-butenal (E), 2-methylbutane, 1-butanol, 1-penten-3-ol, pentanol, 2-ethylfuran, 1,4-dioxane, 3-hydroxy-2-butanone, 1,1-diethoxyethane, 3-methyl-1-butanol, dimethyl disulfide, 2-pentenal (E), toluene, 1-pentanol, hexanal, oxycompound, furfural, 4-hydroxy-4-methyl-2-pentanone, 2-hexenal (E), 1-hexanol, 2-heptanone, cyclohexane, heptanal, 3-methylthiopropanal, α-pinene, camphene, 2-heptenal (E) or (Z), benzaldehyde, dimethyl trisulphide, 1-heptanol, 1-octen-3-ol, 2,3-octanedione, phenol, mevalonic acid, caproic acid, 2-pentylfuran, decane, octanal, 2,4-heptadienal, phenyl acetaldehyde, 2-octenal, (E) acetophenone, 2-octanol, heptadecanoic acid, undecane, linalool, nonanal, α-thujone, β-thujone, 2-ethylhexan carboxylic acid, camphor, 2-nonenal (E), ethylbenzaldehyde, caprylic acid, terpinen-4-ol, naphthalene, α-terpineol, dodecane, decanal, 2,4-nonadienal (E, E), dimethyl tetra sulphide, benzothiazole, carvone, 2-decenal (E), pelargonic acid, 2,4-decadienal (E, Z), thymol, tridecane, geranyl acetone, carvacrol, 2,4-decadienal (E, E), 2-undecenal (E), decane carboxylic acid, dodecanal, penthyl benzaldehyde, undecane-carboxylic acid, 2,6-dibutyl-p-benzoquinone, 1-pentadecen, pentadecane, tridecanal, lauric acid, 1-hexadecene, 2-methylthio benzothiazole, tetradecanal, heptadecane, pentadecanal, myristoleic acid, myristic acid, 9,17-octadecadienal, hexadecanal, isopropyl myristate, pentadecanoic acid, heptadecanal, palmitic acid, 9-octadecenal, octadecanal, linoleic acid, oleic acid, stearic acid.

Determination of the Carboxylic Acids (Volatile Fatty Acids) Content

A content of carboxylic acids (CA) which describes freshness was determined under the research course as follows:

1. To place 25 g of the chopped meat into a 0.75-1.0 liter flask of the distillation apparatus, to add 150 ml of 2% sulphuric acid solution, to mix the flask content, to stopper the flask tightly and to distil using steam until 200 ml of distillate is collected. Simultaneously, a check sample is tested under the same conditions. It is necessary to determine carboxylic acids which may be in the sulphuric acid.

2. To titrate the meat distillate get with 0.1 mol/l sodium hydroxide solution or 0.1 mol/l potassium hydroxide solution (phenolphthalein is as an indicator) and the poultry distillate with 0.1 mol/l potassium hydroxide solution, respectively.

3. A content of the carboxylic acid (in ml) in the meat is calculated using the following formula (2):

$$x = \frac{V_1 - V_2}{2} \times K \qquad (2)$$

where $V_1$—an amount of 0.1 mol/l sodium (or potassium) hydroxide solution consumed for neutralisation of the carboxylic acids contained in 200 ml of the meat extract, in ml, $V_2$—an amount of 0.1 mol/l sodium (or potassium) hydroxide solution consumed for neutralisation of the carboxyl acid contained in 200 ml of the check sample extract, in ml, K—a correction factor of the sodium (or potassium) hydroxide molar concentration (for 1.0-0.1 mol/l sodium (or potassium) hydroxide solution).

4. An content of the carboxylic acids (in mg) in the poultry meat (25 g) is calculated using the following formula (3):

$$x = \frac{4,0 \times (V_1 - V_2) \times K \times 25}{g} \qquad (3)$$

where 4.0—the titre of 0.1 mol/l sodium hydroxide solution, in mg/ml, $V_1$—the amount of 0.1 mol/l sodium hydroxide solution consumed for neutralisation of the carboxylic acids contained in 200 ml of the poultry extract, in ml, $V_2$—the amount of 0.1 mol/l sodium hydroxide solution consumed for neutralisation of the carboxylic acids contained in 200 ml of the check sample extract, in ml, K—the correction factor of the sodium hydroxide molar concentration (for 1.0-0.1 mol/l sodium hydroxide solution);

g—the mass of the sample, g.

Research of Dependence Between Solutions and Sensors

As freshness of the poultry meat is regulated by an amount of the mentioned compounds in the chicken matrix, it is reasonable to assess variations in the general odour quality of the meat headspace, which are influenced by the content of the carboxylic acids produced, and to determine correlation of the sensor response signals of the 'electronic nose' with the values defined by chemical indicators.

In order to achieve this goal, a selected standard scale of the selected acid solutions with concentration of a solution varying from 1 to 12 mg/25 g was prepared. An 'odour' of the headspace of these solutions was assessed by using the e-nose. The samples were analysed, when the analysed solution was poured into a container of 100 ml by filling about one-third of its volume. While measurement assessments were made in the two measurement methods: firstly, the headspace odour resulting in a few minutes was assessed straight after uncovering the container, and secondly, when the container was held uncovered.

Figure 6:
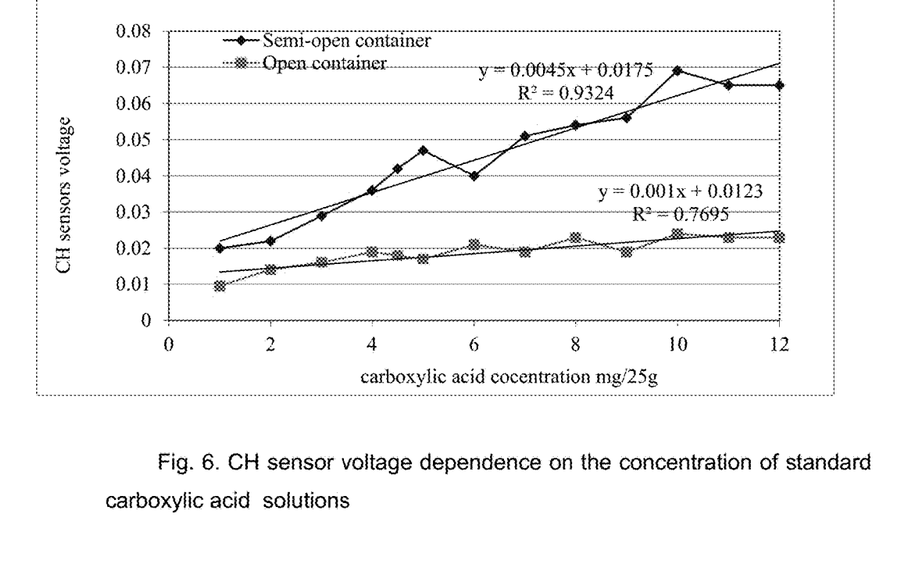
FIG. 6. CH sensor voltage dependence on the concentration of standard CA (carboxylic acid) solutions.

The obtained results indicated that response signal values of the selected sensors, expressed as a voltage (in volts), correlated with the values of concentrations of the analysed solutions by defining in the linear dependences, although while measuring by the second method the dependence was less reliable. It was determined that while measuring the meat freshness without a cover, a distance from the sensors to the surface of the meat should be less than 10 mm. FIG. 6 presents the CH sensor dependence on the headspace odour of standard solutions. $NH_3$ sensor dependences were similar to the CH sensor.

Research of Ageing of Broilers in Poultry Farming Company "Kaišiadorių Paukštynas"

In this research phase, carcass meat of the broilers grown in the Karšiadorys poultry farm and slaughtered three hours ago was tested. For the tests, the meat was prepared by boning and grinding the carcasses. Because of the different chemical and sensory characteristics, samples of the ground breasts and thighs were prepared for the tests. The Soxhlet method showed that the thigh meat was fattier by 4.31%. The samples were aged by keeping them in the refrigerator +4° C., where the temperature in the samples was up to 8° C.

Figure 7:
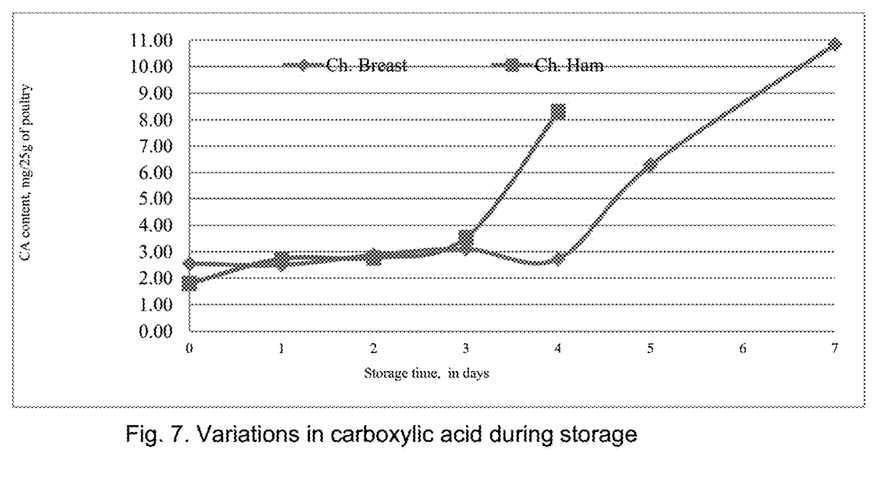
FIG. 7. Variations in CA during storage.
Figure 8:
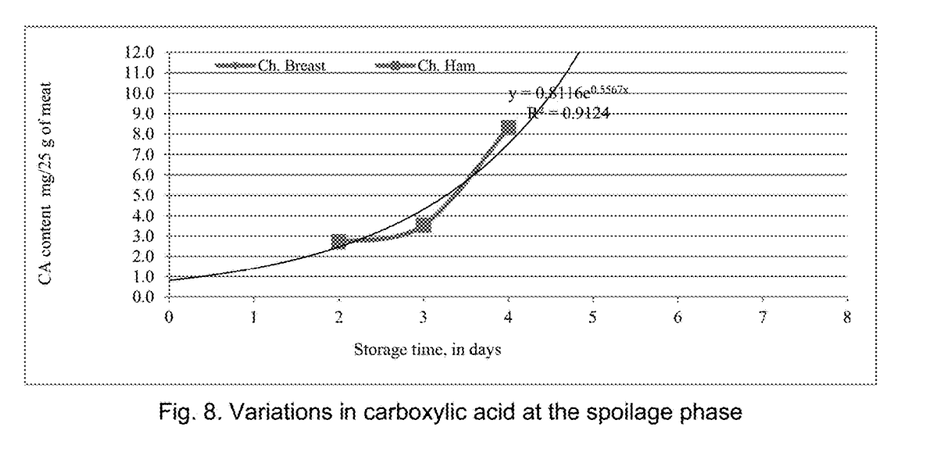
FIG. 8. Variations in CA at the spoilage phase.

Results obtained during the chemical and spectroscopy testing showed that changes occurring in freshness were best described in mathematical dependences by variations of the carboxylic acid changes, as presented in FIG. 7 and FIG. 8.

It is apparent from the results presented that, as expected, spoilage of both the meat samples did not occurred for the first three days, and only after three days the thigh meat began to spoil, i.e. the CA (carboxylic acid) contents began to increase. The breast meat with a lower fat content began to spoil only after four days of ageing and it reached a level of the spoiled meat two days later. Data in FIG. 7 shows that after starting of the spoilage process, its course in both samples was defined by reliable ($R^2=0.9124$ and $R^2=0.9067$) exponential dependencies, i.e. regardless of the anatomical part of the carcass.

During storage of the raw meat, as the pigment oxidation takes place, changes in its colour also occur; therefore, changes of L*a*b* indicators defining the colour were assessed during the ageing. The obtained results are presented in Table 1.

Figure 9:
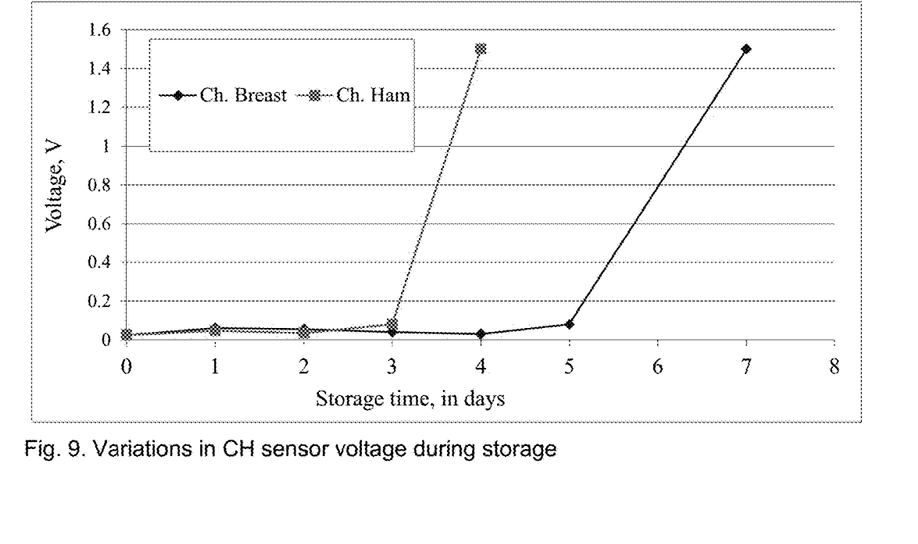
FIG. 9. Variations in CH sensor voltage during storage.

Variations of the CH sensor response signal of the e-nose during ageing of the chicken meat from the Karšiadorys poultry farm are presented in FIG. 9.

It is apparent from the results presented that the sensor signal indication expressed in (V) remained constant during the first days of the testing until the meat remained absolutely fresh under the chemical characteristics and investigators' sensual assessments. Dependences between the CA content and all sensor signals of the e-nose, equations describing them, and reliability coefficients are presented in FIG. 10 and FIG. 11.

Figure 10:
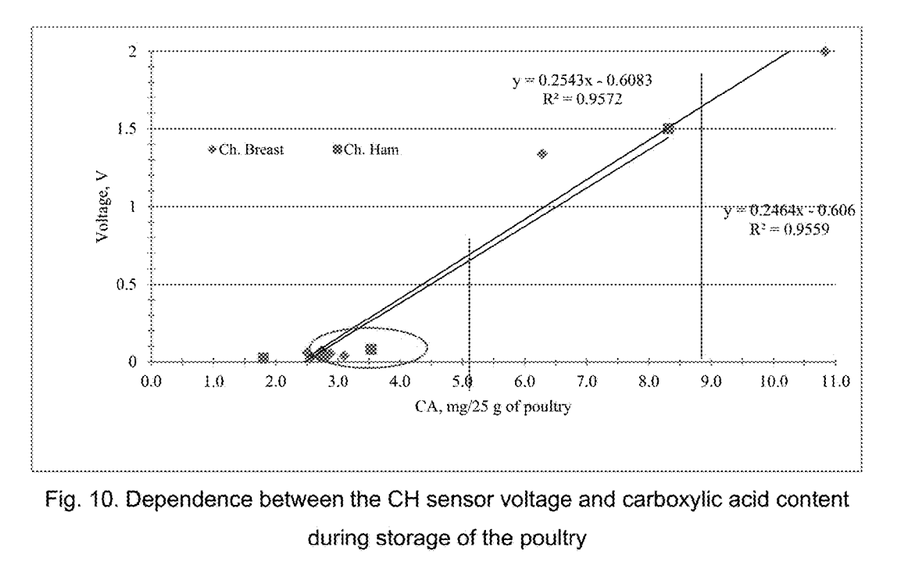
FIG. 10. Dependence between the CH sensor voltage and CA content during storage of the poultry.
Figure 11:
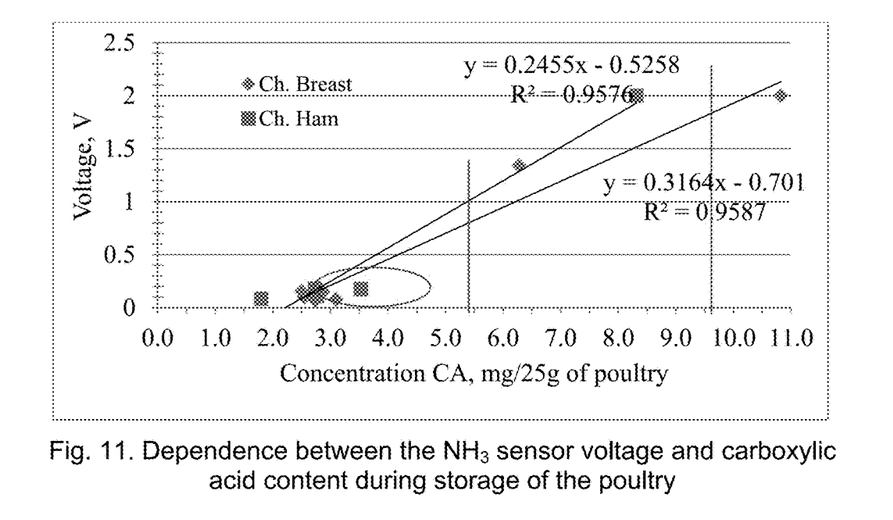
FIG. 11. Dependence between the $NH_3$ sensor voltage and CA content during storage of the poultry.
Figure 12:
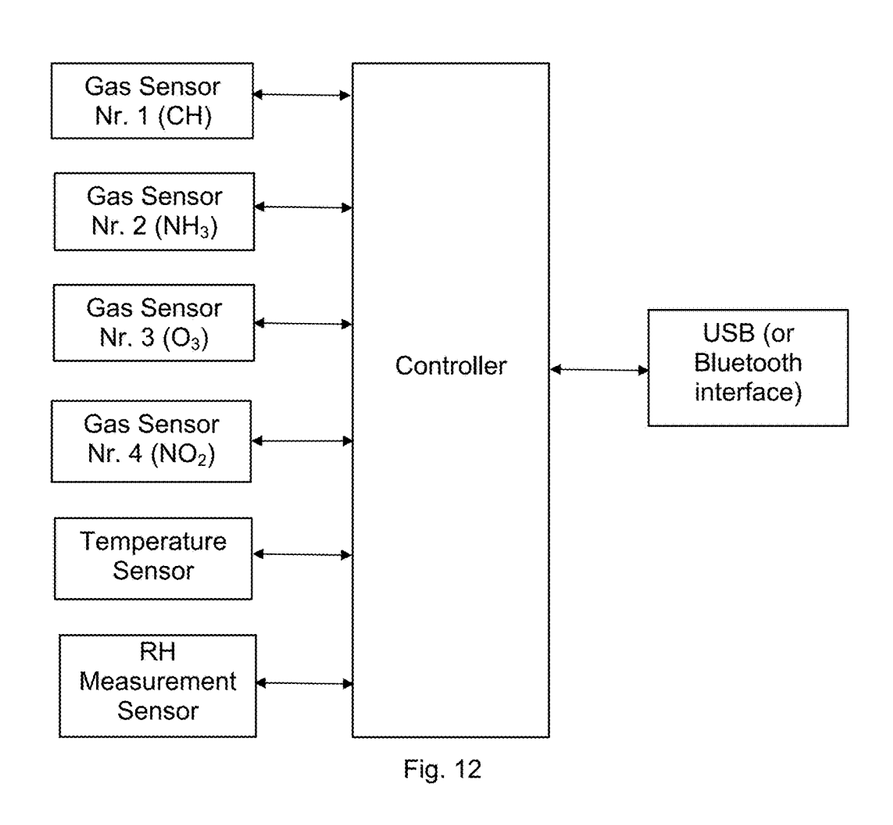
FIG. 12. Structure of the E-nose.
Figure 13:
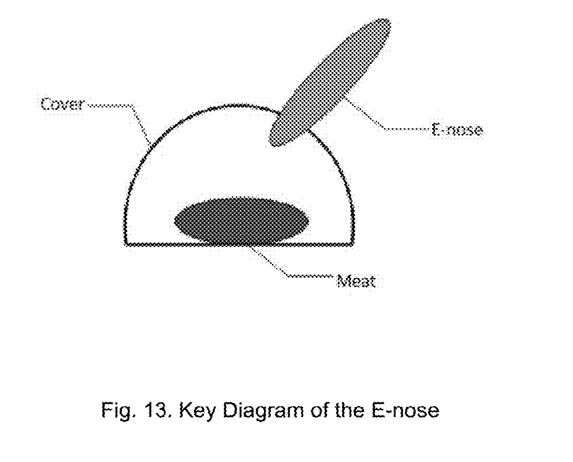
FIG. 13. Key Diagram of the E-nose.
Figure 14:
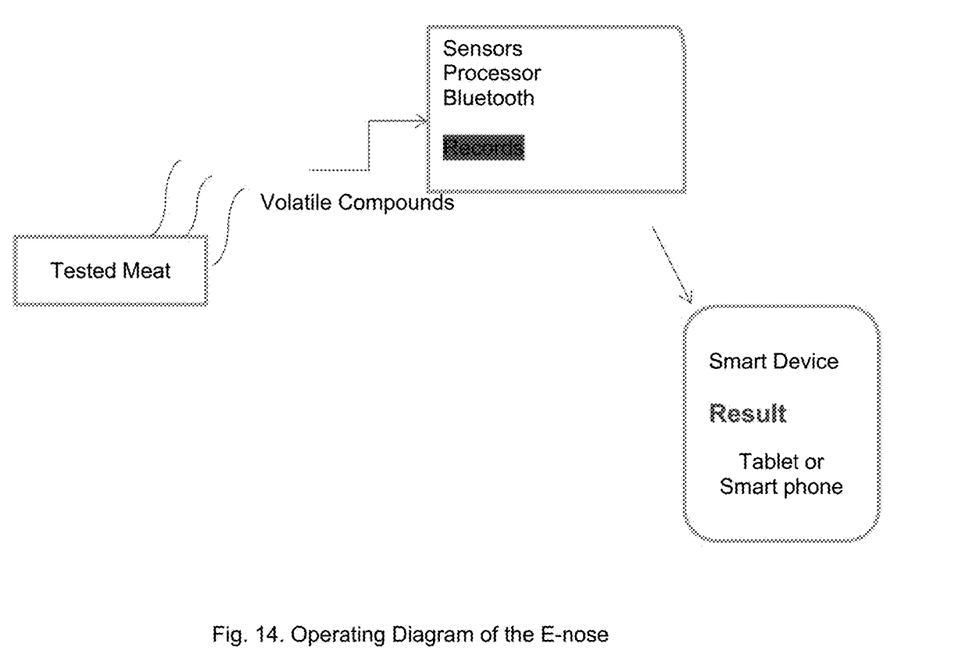
FIG. 14. Operating diagram of the E-nose.
Figure 15:
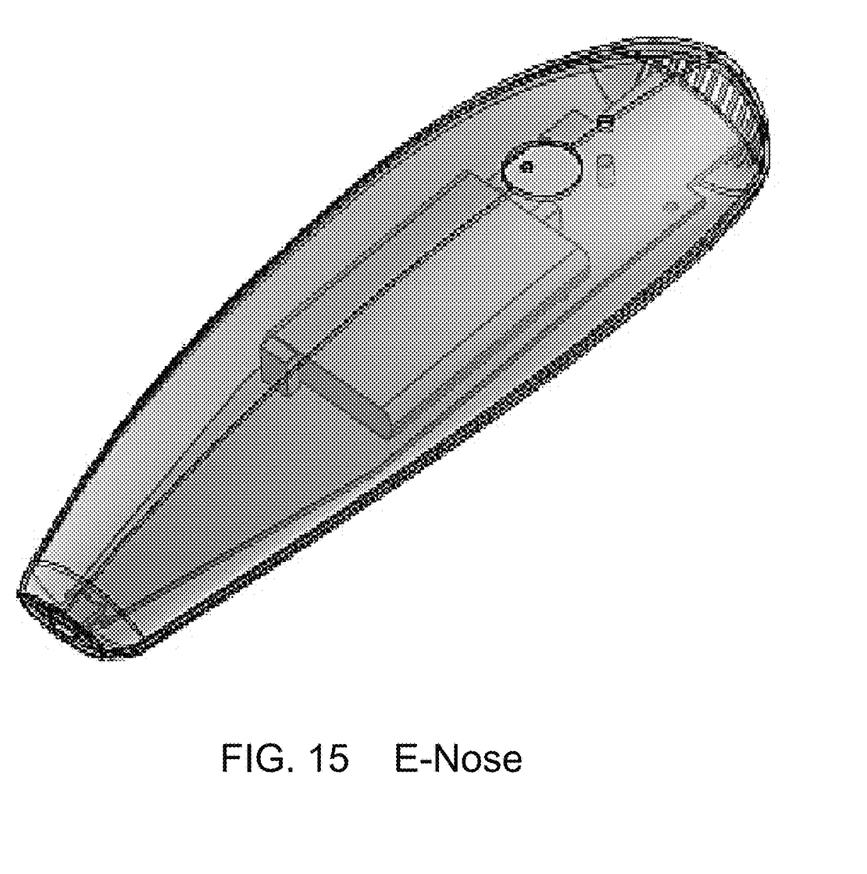
FIG. 15. E-nose.

It can be concluded from the above results that when the meat remained fresh under indications of the CA content, the CH sensor signal voltage did not exceed the value of 0.055. A response signal intensity of the $NH_3$ sensor is slightly higher −0.182, and it can reach a value of 0.6 during testing of freshness of the suspicious chicken meat.

During storage of the chicken meat, the CA variations had a clear tendency to increase, and marginal carboxylic acid values of 'suspicious freshness' and 'spoiled' meat correlated with the assessors' sensual senses.

Carboxylic acid variations, as well as regulated concentrations directly, by reliable linear dependences correlated with the sensor voltage values.

The invention claimed is:

1. A portable electronic nose used for determining meat freshness, said electronic nose comprising: a gas sensor system including at least two metal-oxide semiconductor sensors configured to measure a value of $NH_3$, and a value of CH, and configured to record changes in values of a concentration of volatile organic compounds released during a meat spoilage; a processor configured to receive and process incoming gas sensor output signals from the gas sensor system and convert them into a sequence of electrical signals based on variations in a value of concentrations of the volatile organic compounds detected in a headspace above a tested meat; wherein a variation of output signals from the gas sensor system after storage of the meat to obtain an initial value of $NH_3$ and an initial value of CH and provide a comparison of each of the values to threshold levels to determine meat freshness levels and to send the electrical signals to a Bluetooth device which transmits the signals to a mobile device containing software that processes the electrical signals to determine a variation of output signals from the gas sensor system or receives the results of the comparison from the processor; wherein the mobile device further comprising a video output device to display the meat freshness level of the tested meat.

2. The portable electronic nose according to claim 1, further including an optional tool shielding extraneous odors and creating the headspace.

3. The portable electronic nose according to claim 2, wherein the tested meat is chicken.

4. The portable electronic nose according to claim 1, wherein the sensor system is configured to record variations in the values of the concentrations of the volatile organic compounds released by the meat during spoilage.

5. The portable electronic nose according to claim 1, wherein the tested meat is chicken.

6. The portable electronic nose according to claim 1, wherein the gas sensor system includes at least two metal-oxide semiconductor sensors configured to measure the value of NH3, and the value of CH, and is configured to record changes in the value of the concentrations of the volatile organic compounds; and the processor is configured to receive and process incoming signals from the gas sensor system and to convert incoming signals into a sequence of electrical signals based on the value of variations in concentrations of the volatile organic compounds from the tested meat sample to threshold levels to determine meat freshness levels.

7. A method for determining meat freshness by using an electronic nose, wherein the electronic nose comprises: a gas sensor system including at least two metal-oxide semiconductor sensors configured to measure a value of $NH_3$, and a value of CH, and configured to record changes in values of concentrations of volatile organic compounds released during a meat spoilage; a processor configured to receive and process incoming gas sensor output signals from the gas sensor system and convert them into a sequence of electrical signals based on variations in the value of concentrations of the volatile organic compounds detected in a headspace above a tested meat; wherein a variation of output signals from the gas sensor system after storage of the tested meat to obtain an initial value of $NH_3$ and an initial value of CH and provide a comparison of each of the values to threshold levels to determine meat freshness levels, and to send the electrical signals to a Bluetooth device which transmits signals to a mobile device containing a software program that processes the electrical signals to determine the variation of output signals from the gas sensor system of the tested meat and an initial value of the value of $NH_3$ and an initial value of CH or receives the results of the comparison from the processor; the mobile device further comprising a video output device, wherein the mobile device processes signals from the electronic nose and displays the meat freshness measurement results; wherein a variation of gas sensor output signals indicates that changes have taken place in the concentrations of the volatile organic compounds in the headspace above a tested meat sample; wherein the method comprises: a) measuring variations in a value of concentrations of volatile organic compounds in a sample headspace using the gas sensor system; and b) transmitting a gas sensor system signal to the processor from the gas sensor system and to convert incoming signals into a sequence of electrical signals based on variations in concentrations of the volatile organic compounds from the tested meat sample to threshold levels to determine a meat freshness level.

8. The method for determining meat freshness according to claim 7, further comprising, placing the meat sample to be tested for freshness under a tool shielding extraneous odors and creating a defined headspace over the meat sample to be tested.

9. The method for determining meat freshness according to claim 8, wherein the tool, shielding extraneous odors and creating a defined headspace, comprises a container with a lid, and one of, a cover or funnel tip-cover to isolate sensors from environment gases.

10. The method for determining meat freshness according to claim 9, wherein the sensor system records the variations in concentrations of the volatile organic compounds maximum within 2 minutes.

11. The method for determining meat freshness according to claim 9, wherein the tested meat is chicken.

12. The method for determining meat freshness according to claim 9, wherein a distance from the gas sensors to the surface of the meat sample is less than 10 mm while measuring in an open space over the meat sample.

\* \* \* \* \*